(12) United States Patent
Lieberman

(10) Patent No.: US 6,667,807 B2
(45) Date of Patent: Dec. 23, 2003

(54) SURFACE PLASMON RESONANCE APPARATUS AND METHOD

(75) Inventor: Robert A. Lieberman, Torrance, CA (US)

(73) Assignee: Optech Ventures, LLC, Torrance, CA (US)

(*) Notice: Subject to any disclaimer, the term of this patent is extended or adjusted under 35 U.S.C. 154(b) by 209 days.

(21) Appl. No.: 09/823,858

(22) Filed: Mar. 30, 2001

(65) Prior Publication Data

US 2002/0140937 A1 Oct. 3, 2002

(51) Int. Cl.[7] .......................... G01N 21/55; G01N 21/63
(52) U.S. Cl. ............................ 356/445; 356/136
(58) Field of Search .................. 356/445, 136

(56) References Cited

U.S. PATENT DOCUMENTS

| | | | | |
|---|---|---|---|---|
| 4,451,123 A | * | 5/1984 | McNeill et al. ............. 359/263 |
| 4,767,719 A | * | 8/1988 | Finlan ........................ 436/501 |
| 5,155,617 A | * | 10/1992 | Solgaard et al. ............. 359/245 |
| 5,272,022 A | * | 12/1993 | Takami et al. ............... 429/331 |
| 5,351,127 A | * | 9/1994 | King et al. .................. 356/445 |
| 5,451,980 A | * | 9/1995 | Simon et al. .................. 345/88 |
| 5,926,284 A | * | 7/1999 | Naya et al. .................. 356/445 |
| 6,482,988 B2 | * | 11/2002 | Fukushima et al. ........... 568/22 |
| 6,504,651 B1 | * | 1/2003 | Takatori ..................... 359/640 |

* cited by examiner

Primary Examiner—Michael P. Stafira
(74) Attorney, Agent, or Firm—Lawrence S. Cohen

(57) ABSTRACT

A surface plasmon resonance device includes a metal thin film, a dielectric thin film on an optical member and, in addition, an electro-optically active thin film either between the metal thin film and the dielectric thin film or between the optical member and the metal thin film. The electro-optically active thin film is subject to a voltage which is varied to tune the resonance condition of the device.

14 Claims, 2 Drawing Sheets

SURFACE PLASMON RESONANCE APPARATUS AND METHOD

FIELD OF THE INVENTION

The invention relates to surface plasmon resonance devices and in particular to application of surface plasma resonance devices to biosensors.

BACKGROUND

Surface plasmon resonance (SPR) is used to examine the optical properties of a thin film which is under investigation. Surface plasmon resonance has been used, for example, in biosensor apparatus for reading thickness changes in binding processes on microarray biochips. The use of SPR permits these changes to be detected as changes in local optical reflectivity.

SPR is a useful technique because the effect being studied only exists at surfaces, that is, at interfaces between a metal and dielectric materials.

Known SPR devices, comprising a metallic layer and a recognition layer deposited on a prism or waveguide, detect changes in the plasmon resonance angle when an analyte changes the recognition layer's refractive index.

Known SPR apparatus has certain problems. One problem is that the apparatus implements an SPR technique which is a steady state technique. That is, the apparatus looks for a dark spot in reflectivity by moving a light source or by implementing multiple angles. Known SPR techniques have limited dynamic range and must be operated within limited refractive index values. The fundamental SPR event in known devices also cannot be modulated. Their sensitivity is limited.

SUMMARY OF THE INVENTION

The invention is an improvement in SPR apparatus and methods. The invention resides in the inclusion of, for example, an electro-optically active or thermally controlled layer that can be used to "tune" the plasmon resonance, to modulate it, or to gate it. The invention is applicable to surface plasmon resonance biosensing by active multilayer detection. Active multilayer devices using the principles of the invention enable the use of SPR techniques in numerous applications, for example, in micro-assays for diagnostics, for drug development or for biotechnology experiments, by enhancing sensitivity and range of operation while simultaneously shrinking the size requirements of SPR devices. Other controlled layers may be any such layer the refractive index of which can be controlled.

DETAILED DESCRIPTION

Figure 1:
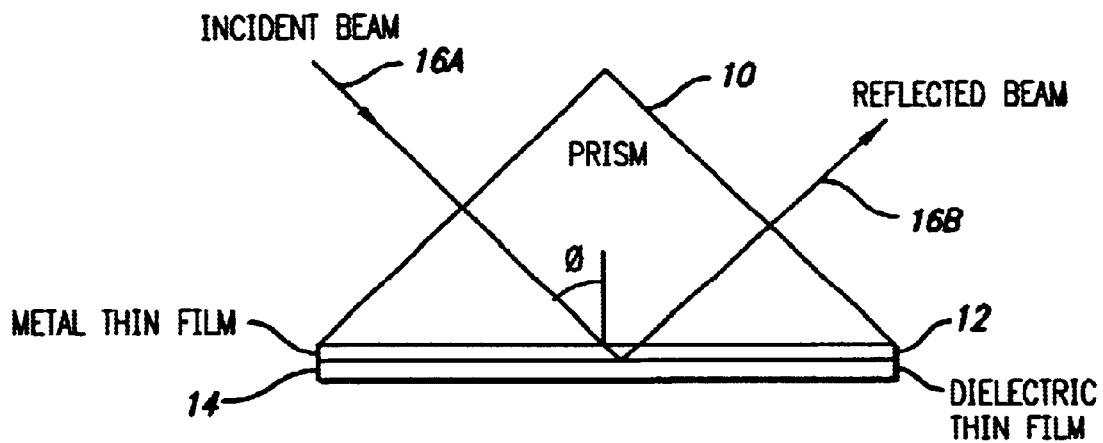
FIG. 1 shows a prior art surface plasmon resonance structure.

FIG. 1 shows a type of surface plasmon resonance device of the prior art. A total internal reflection (TIR) prism 10 has on it a metal thin film 12 and a dielectric thin film 14. Since surface plasmon waves propagate in TM (transverse magnetic) mode, the light beam 16A is TM-polarized light, entering at an angle to produce total internal reflection and an associated evanescent wave. Variations of this device often use metal coated glass slides placed against the prism, so that the surface of the slide is the TIR surface rather than the prism surface itself as the TIR surface. The technology of prior art surface plasmon resonance (SPR) has been developed and published in the literature, is known to those skilled in the art and need not be recited in detail here other than as needed to understand the present invention.

SPR devices are used to measure refractive index and refractive index changes of a thin layer near a solid surface. In the context of biosensors, the biological material is placed on a surface defining a thin layer referred to as a biorecognition layer. The goal is to measure changes in thickness of biological material which comprises the biorecognition layer. During the biosensing procedure, the biological material which constitutes the biorecognition layer undergoes changes in properties, the specifically relevant changes being in optical thickness. SPR is sensitive to changes in optical thickness, or refraction index changes. Therefore SPR devices are useful for biosensing. However, SPR devices in accordance with the principles of this invention are more sensitive than prior art SPR devices and thus can measure relatively smaller changes in refractive index than can be measured by prior art devices. The smaller the change in refractive index that can be measured, the smaller are the changes in the biorecognition layer that can be measured. Also prior art devices are limited in the frequency in which sequential measurements can be made.

Figure 2:
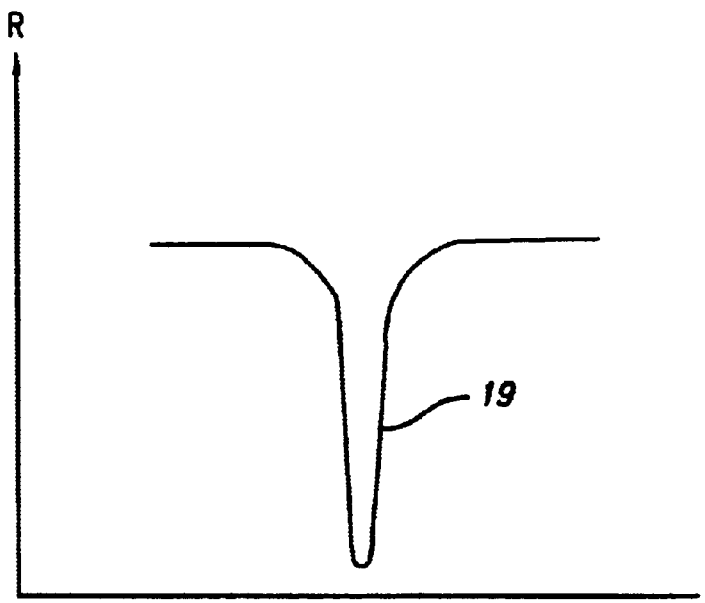
FIG. 2 is a typical SPR sensitivity curve.

A typical SPR sensitivity curve is shown in FIG. 2; where the horizontal axis can be refractive index, light incidence angle or wavelength, and the vertical axis is reflected light intensity.

By using the principles of the present invention the ability of SPR devices to collect biological information in a biological binding process can be increased. In particular, due to the greater sensitivity and range being available, relatively small changes in optical thickness can be detected, greater accuracy of optical thickness can be measured and a wider range of optical thicknesses can be measured.

The technical problem addressed by the present invention is to extend the sensitivity of SPR devices by providing a control to modulate the refractive index of the SPR. According to one embodiment of the invention, an electro-optically active layer is employed the refractive index of which is modulated according to an impressed voltage. The voltage can range from DC to AC up to any practical frequency such as into the gigahertz range. The sensitivity of SPR devices is increased by modulating the voltage to vary the refractive index around a set point. It is advantageous to modulate the voltage about some selected or variable level of AC voltage.

In addition to increasing sensitivity of an SPR sensing device, apparatus in accordance with the present invention can increase range of the SPR device. To increase range, as the refractive index starts to change, we take advantage of the fact that the reflectance (R) starts to change with it. A voltage applied to the electro-optically active layer of the invention shifts the curve 19 of FIG. 2. Therefore it is possible by applying a voltage signal which shifts the curve in a manner to maintain the resonance condition that gives the highest sensitivity.

Also according to the principles of the invention, it is possible to do null point detection. That is to say, it is possible to set the apparatus to start at a given point on the refractive index line of FIG. 2, where there is a minimum or no light. As light begins to appear due to changes in the biorecognition layer, it is possible to change the refractive index of the SPR device by changing the voltage impressed on the electro-optically active layer to come back to the minimum reflectivity condition.

Also, the voltage change that produces the null condition is a direct measurement of the change in refractive index that has occurred in the biorecognition layer, that is the change in thickness of the biological material. In this way, the change in thickness can be measured continuously or at intermediate times in the biological experiment, and the time rate of change can be calculated, all of which can enhance the biological information available.

Also, if the electro-optically active layer is set up to detect minimum light, that is its refractive index is controlled via a DC voltage to get minimum light, and a small modulation voltage is added, oscillating at frequency f, the detector will see a signal at 2 f (according to the principle of frequency doubling). If this signal is used in a feedback loop to maximize the 2 f signal, the result will be very fast automatic locking at the minimum light condition, and the voltage change necessary to achieve the locking will be a direct measurement of the change in biological thickness. Similarly the rate of change can be measured in very small increments.

Figure 3:
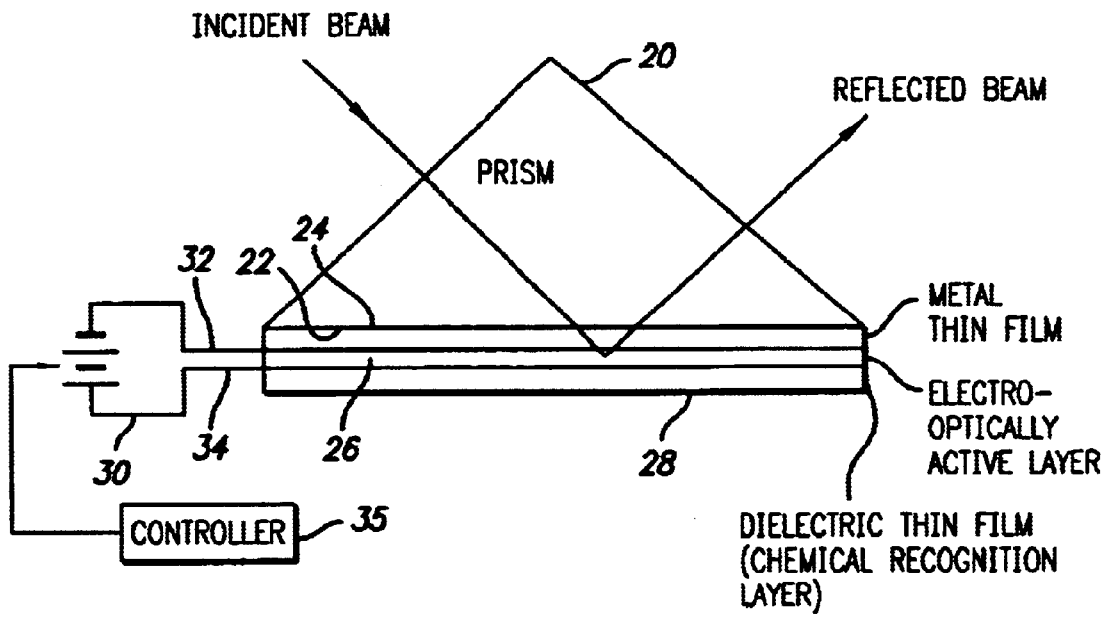
FIG. 3 shows a surface plasmon resonance structure which embodies the invention.
Figure 4:
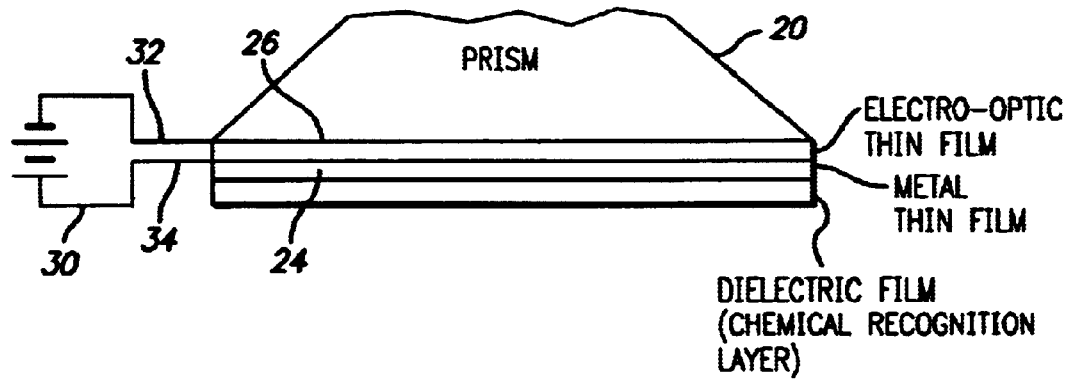
FIG. 4 shows an alternative surface plasmon resonance structure which embodies the invention.

FIGS. 3 and 4 show structures that implement the invention. Specifically, FIG. 3 shows a TIR structure, shown as a TIR prism 20, which has on its surface 22 a metal thin film 24, an electro-optically active thin film 26, dielectric thin film 28, also referred to as a chemical recognition layer 28, and an electric field generator 30. Generator 30 is attached by lines 32, 34 to the electro-optically active thin film 26. FIG. 4 shows a similar structure, except that the electro-optically active thin film 26 is between the TIR prism 20 and the metal thin film 24. In each of the embodiments of FIGS. 3 and 4 the electro-optically active thin film 26 is adjacent the metal thin film 24. The dielectric thin film 28 (chemical recognition layer) is distal from the TIR prism 20, that is with both the metal thin film 24 and the electro-optically active thin film 26 between the TIR prism 20 and the dielectric thin film 28.

Although the TIR prism 20 is shown as the source of TIR incident light, other means of providing a totally internally reflected beam and an evanescent wave could be employed.

The electric field generator 30 is preferably selectably or controllably variable so that by varying the electric field on the electro-optically active thin film 26 the plasmon resonance can be modulated. FIG. 3 shows a controller 35 for controlling generator 30. Controller 35 may be any such device as, for example, a microprocessor for controlling the electric field.

The effect of adding the electro-optically active thin film adjacent to the metal thin film is to allow a resonance condition to be scanned or modulated without the need for angle or wavelength scanning. This makes DC null-point detection possible as the sensor could be maintained in the plasmon resonance condition by controlling the refractive index of the active layer in a feedback loop whose "error voltage" would give direct indication of changes in the refractive index of the dielectric layer.

Alternatively, the index of the modulation layer could be scanned at a fixed or variable frequency, and changes in the refractive index of the dielectric layer could be detected as changes in the amplitude of the second harmonic light signal.

Another advantageous use of the invention is that it allows for tuning the plasmon sensor response to the refractive index range of interest. For example refractive indices of chemical recognition systems cover a wide range of values, and, ordinarily, changing recognition layers would necessitate the engineering of a new metal film, or even the use of a new prism. Use of the intermediate tunable electro-optically active layer alleviates this problem, since application of a DC voltage to the electro-optically active layer biases the multilayer structure in such a way as to compensate for changes in the basic refractive index of the recognition layer.

The preferred materials for the electro-optically active layer are:
Polyimide
Polyaniline
Poly (N-benzyl aniline)
Poly (N-napthyl aniline)
Poly (2-ethoxyaniline)
Poly (diarylaniline)
Poly (DR1-MMA)

The most preferred material is poly (DR1-MMA) which is an abbreviated term for poly (disperse red 1 methacrylate-co-methyl methacrylate).

While there are shown and described herein certain specific combinations embodying the invention for the purpose of clarity of understanding, the specific combinations are to be considered illustrative in character, it being understood that only preferred embodiments have been shown and described. It will be manifest to those of ordinary skill in the art that certain changes, various modifications and rearrangements of the features may be made without departing from the spirit and scope of the underlying inventive concept and concepts and that the present invention is not limited to the particular forms herein shown and described except insofar as indicated by the scope of the appended claims and equivalents thereof.

What is claimed is:

1. Apparatus comprising an optical structure having a planar surface and means for directing polarized light through said optical structure at said surface at an angle to obtain total internal reflection from said surface, said apparatus comprising a metallic layer and a recognition layer on said surface, said apparatus also including a voltage responsive layer for changing the refractive index thereof in a manner to vary the penetration of said light into said recognition layer, including a voltage source connected to said voltage responsive layer and including control means for varying the voltage impressed across said voltage responsive layer in a manner to modulate the refractive index of said voltage responsive layer about a set point.

2. Apparatus as in claim 1 wherein said set point is a null point.

3. Apparatus as in claim 1 including a feedback loop responsive to a minimum light intensity signal for changing the voltage impressed upon said voltage responsive layer to maintain a minimum light intensity condition.

4. Apparatus as in claim 2 also including output means for detecting the light intensity signal reflected from said surface.

5. A method for the modulation of plasmon resonance in a surface Plasmon resonance device including a total internal reflection element, a thin metallic layer and a recognition layer, said method comprising the steps of forming adjacent to said metallic layer, an electro-optically active layer and impressing across said electro-optically active layer a voltage signal for varying the index of refraction thereof about a set point.

6. A method as in claim 5 wherein said voltage is varied about a null point.

7. A method as in claim 5 wherein said voltage is varied in a manner to maintain a reflected light signal at a minimum intensity.

8. Apparatus comprising an optical structure having a planar surface and means for directing polarized light through said optical structure at said surface at an angle to obtain total internal reflection from said surface, said apparatus comprising a metallic layer and a recognition layer on said surface, said apparatus also including a voltage responsive layer for changing the refractive index thereof in a manner to vary the penetration of said light into said recognition layer, said recognition layer comprising a dielectric film and said voltage layer is located between said metallic layer and said dielectric film.

9. Apparatus comprising an optical structure having a planar surface and means for directing polarized light through said optical structure at said surface at an angle to obtain total internal reflection from said surface, said apparatus comprising a metallic layer and a recognition layer on said surface, said apparatus also including a voltage responsive layer for changing the refractive index thereof in a manner to vary the penetration of said light into said recognition layer, said voltage responsive layer comprising an electro-optically active thin film of a material selected from the class consisting of Polyamide, Polyanaline, Poly (N-benzyl aniline), Poly (2-ethoxyanaline), Poly (diarylaniline) and Poly (DRI-MMA).

10. Apparatus comprising an optical structure having a planar surface and means for directing polarized light through said optical structure at said surface at an angle to obtain total internal reflection from said surface, said apparatus comprising a metallic layer and a recognition layer on said surface, said apparatus also including a voltage responsive layer for changing the refractive index thereof in a manner to vary the penetration of said light into said recognition layer, said voltage responsive layer comprising an electro-optically active thin film of a material comprising Poly (DRI-MMA).

11. A method for determining the change in thickness of a specimen over time using a surface plasmon resonance device including a total internal reflection element, a thin metallic layer and a recognition layer containing the specimen, said method comprising the steps of, forming adjacent to the metallic layer an electro-optically active layer;

impressing across the electro-optically active layer a voltage for varying the index of refraction of the electro-optically active layer;

setting the voltage to a first null point at which there is a minimum of reflectivity of the surface plasmon resonance device to establish a voltage level for the first null point;

at a later time upon a change in the reflectivity of the first null point indicating a change in the index of refraction of the specimen, changing the impressed voltage to establish a new null point of minimum reflectivity whereby the change in the impressed voltage to return to a null point is a direct measure of the change in refractive index of the specimen; and comparing the impressed voltage of the first null point to the impressed voltage of the new null point and processing the comparison to determine the thickness change of the specimen.

12. The method of claim 11 further comprising controlling the electro-optically active layer to detect minimum light by use of a DC voltage and adding a small modulation voltage, oscillating at a selected frequency, f, and providing a frequency detector for detecting change in the signal as 2 f.

13. The method of claim 11 further comprising using the signal as a feedback loop to maximize the 2 f signal whereby very fast automatic locking at the minimum light condition will result and the voltage necessary to achieve the locking will be a direct measurement of the change in thickness of the specimen.

14. The method of claim 11 further comprising using sequential measurements over time determining the rate of change of thickness of the specimen.

* * * * *